United States Patent
Giglio et al.

(10) Patent No.: US 7,924,431 B2
(45) Date of Patent: Apr. 12, 2011

(54) METHOD OF MEASURING PROPERTIES OF PARTICLES AND CORRESPONDING APPARATUS

(75) Inventors: Marzio Giglio, Milan (IT); Marco Alberto Carlo Potenza, Milan (IT)

(73) Assignee: Universita' Degli Studi Di Milano, Milan (IT)

( * ) Notice: Subject to any disclaimer, the term of this patent is extended or adjusted under 35 U.S.C. 154(b) by 389 days.

(21) Appl. No.: 11/993,727

(22) PCT Filed: Jun. 22, 2005

(86) PCT No.: PCT/IT2005/000362
§ 371 (c)(1),
(2), (4) Date: May 22, 2008

(87) PCT Pub. No.: WO2006/137090
PCT Pub. Date: Dec. 28, 2006

(65) Prior Publication Data
US 2010/0141945 A1 Jun. 10, 2010

(51) Int. Cl.
*G01B 9/02* (2006.01)
(52) U.S. Cl. ............................................ 356/496
(58) Field of Classification Search .................. 356/450, 356/496, 498
See application file for complete search history.

(56) References Cited

U.S. PATENT DOCUMENTS
6,219,138 B1 * 4/2001 Swanson et al. .............. 356/336
(Continued)

FOREIGN PATENT DOCUMENTS
WO WO 2005/083389 A1 9/2005

OTHER PUBLICATIONS
Bassini, Alessandra et al. "Interferometric system for precise submicrometer particle sizing." Applied Optics, Optical Society of America, vol. 35 No. 31. Nov. 1997.
(Continued)

*Primary Examiner* — Hwa S. A Lee
(74) *Attorney, Agent, or Firm* — Merchant & Gould P.C.

(57) ABSTRACT

A method of measuring properties of particles includes generating a beam of radiation (IW); illuminating with the beam (IW) an observation region (MR) which is transited by a particle (B). A portion of the beam (IW) gives rise to radiation (SW) which is scattered by scattering interaction with the particle (B), and another portion (TW) is transmitted substantially undisturbed through the observation region (MR). In a detection plane (M), a plurality of radiation intensity values are detected which are determined by the interference between the scattered radiation (SW) and the transmitted radiation (TW). The detection of the radiation intensity values in the detection plane (M) is carried out according to a time sequence of acquisitions corresponding to successive transit positions of the particle through the observation region (MR). On the basis of the time sequence of acquisitions, the trend of a parameter of asymmetry of the distribution of the plurality of radiation intensity values with respect to the optical axis (z), due to the successive transit positions of the particle (B), is determined as a function of time. Depending on the trend of the parameter of asymmetry determined as a function of time, the trends of phase delay and amplitude of the scattered radiation (SW) with respect to the transmitted radiation (TW) are determined as a function of time, and the properties of the particle (B) are determined on the basis of the trends of the phase delay and amplitude of the scattered radiation (SW) as a function of time.

10 Claims, 5 Drawing Sheets

U.S. PATENT DOCUMENTS 7,268,874 B2 *  9/2007  Brogioli et al. ............... 356/336
2004/0239932 A1  12/2004  Brogioli et al.

OTHER PUBLICATIONS

Taubenblatt, M.A., et al. "Measurement of the size and refractive index of a small particle using the complex forward-scattered electromagnetic field." Applied Optics, Optical Society of America, vol. 30 No. 33. Nov. 1991.

Pralle et al. "Three-Dimensional High-Resolution Particle Tracking for Optical Tweezers by Forward Scattered Light." Microscopy Research and Technique, vol. 44 pp. 378-386. 1999.

Hirleman, Dan E. "Laser Technique for simultaneous particle-size and—velocity measurements." Optics Letters vol. 3, No. 1, 1978.

* cited by examiner

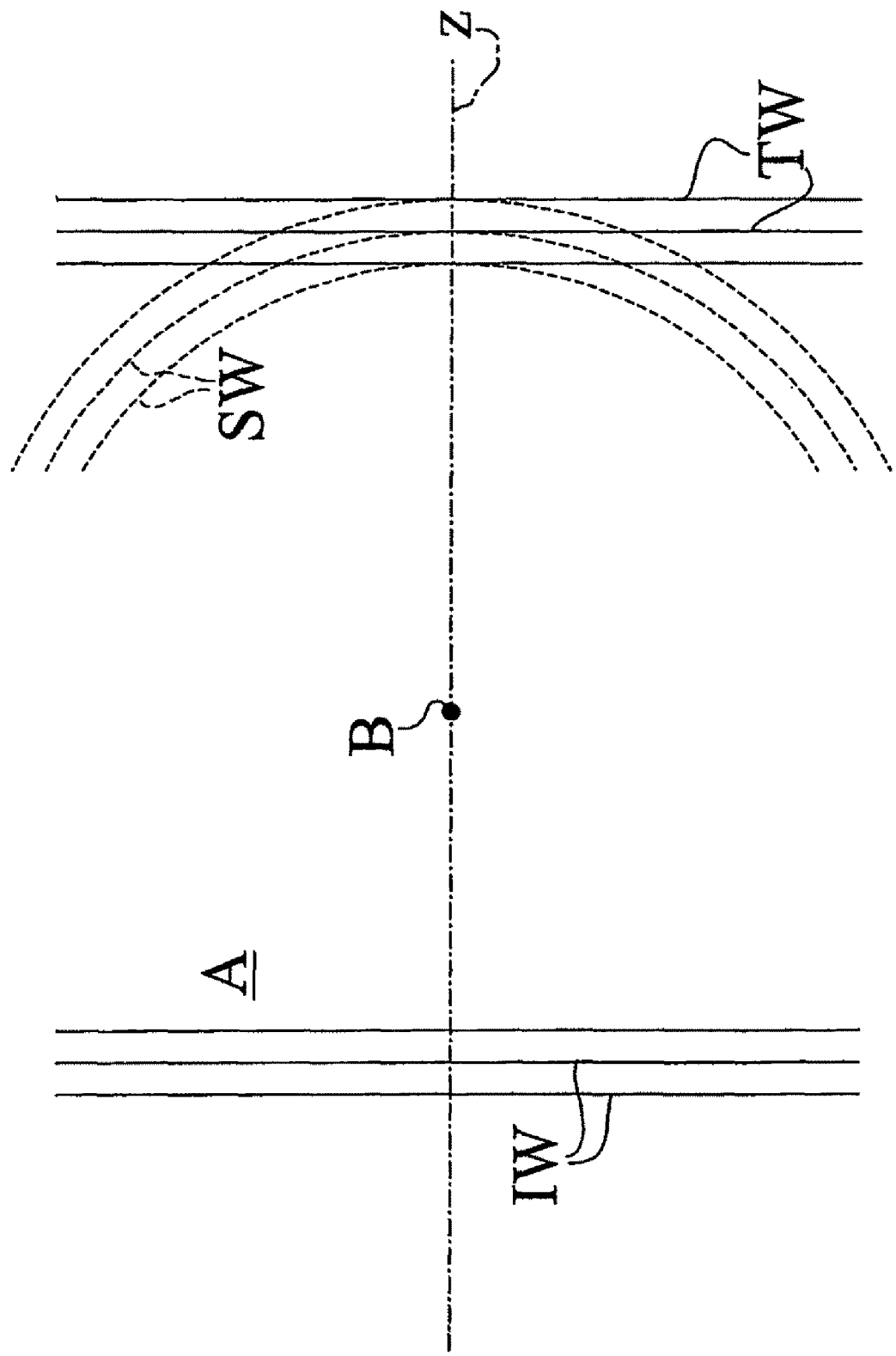

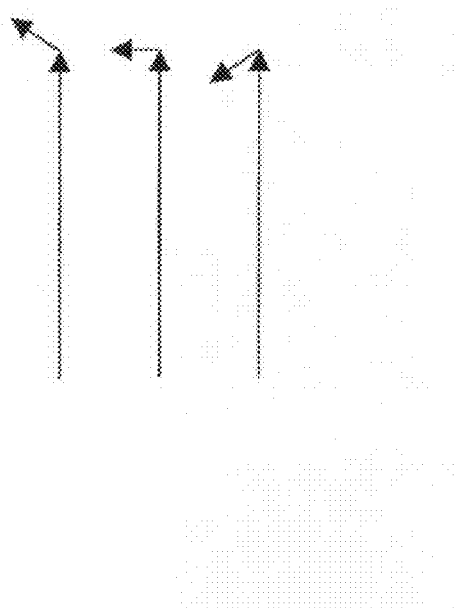
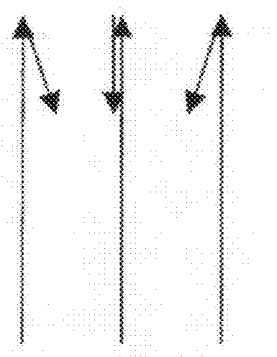
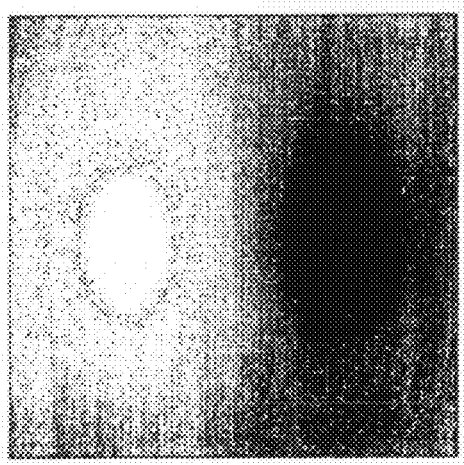
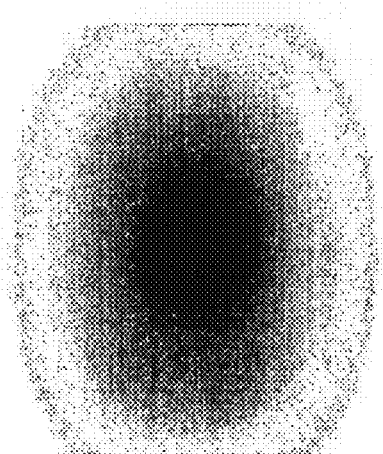
Fig. 2a
Fig. 2b

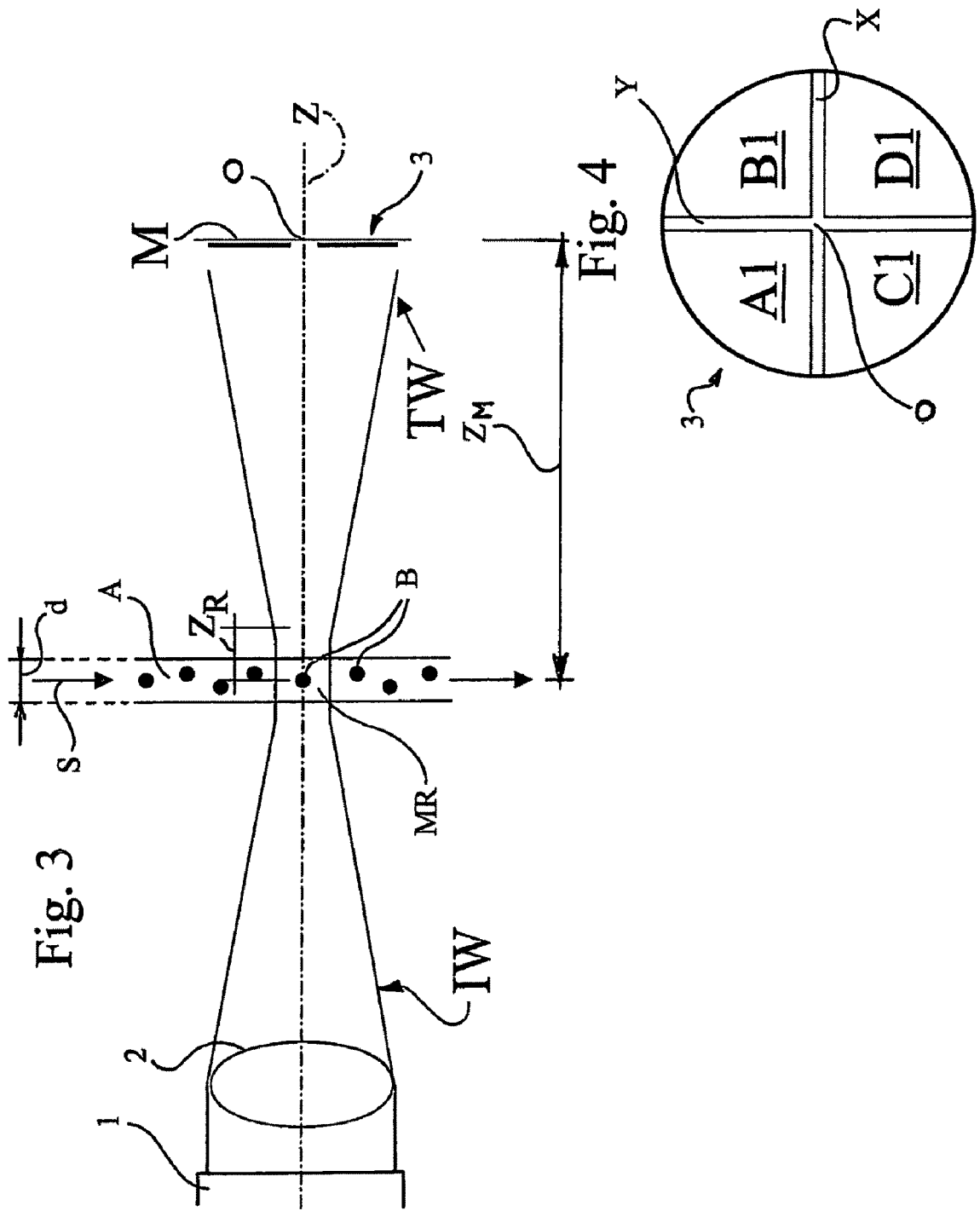

METHOD OF MEASURING PROPERTIES OF PARTICLES AND CORRESPONDING APPARATUS

The present invention relates to a method of measuring properties of particles of the type described in the preamble to claim 1.

For the determination of the properties of the particles, the method is based on a wave-scattering, or diffusion, process.

More precisely, the present invention relates to a method for the determination of properties of single particles by means of analysis of the intensity distribution resulting from interference between the wave scattered by a particle and the fraction of the incident wave which propagates undisturbed.

Conventional light-scattering techniques for the determination of properties of particles or materials such as information on their size, shape, and structure are based on measurement of the distribution of the intensity of the radiation scattered by one or more particles. In case the particle size is less than the wavelength, this method is however limited by the fact that the intensity of the scattered wave is proportional to the sixth power of the radius of the particle, and therefore the intensity of the scattered radiation decreases very rapidly with decreasing particle size. In general, information on the phase of the scattered waves is lost. However, the phase difference between the scattered wave and the incident wave contains valuable information relating the particle size, in particular in the case of particles with size less than the wavelength.

The present invention is intended to provide a method and apparatus for the measurement of properties of particles which is capable to overcome the aforesaid drawbacks.

To this end, the method and apparatus according to the present invention are based on the determination of phase and amplitude of the scattered wave according to the following physical principle which is illustrated with reference to FIG. 1a.

Let's consider an electromagnetic plane wave IW which propagates in a homogeneous medium A along a direction z and is incident on a particle B. The medium A and the particle B (which may be, for example, a particle in a fluid or even a bubble in a transparent, solid or liquid material) have refractive indices of $n_A$ and $n_B$, respectively, at the frequency of the wave IW.

The particle B becomes the source of a spherical electromagnetic wave SW, known as scattered wave. In a plane (not shown) disposed at a predetermined distance from the particle along the axis z, the interference between the transmitted field TW and the scattered field SW gives rise to an interference pattern with circular fringes, which are concentric around the projection of the position of the particle in the plane. The luminous fringes are determined by the constructive interference between the scattered wave and the transmitted wave. The diameter $d_n$ of the nth fringe is scaled as $an^2+b$, where a depends only on the wavelength and on the distance between particle and detection plane and b, which is commonly known as fractional order at the centre, is linked to the phase difference between scattered spherical wave and transmitted plane wave in the forward direction. For example, if the two waves are in phase, then $b=0$ and an interference maximum is observed at the centre of the system of fringes.

Apart from the geometrical structure of the fringes, modulation depth is another very important parameter, which is determined by the ratio between scattered and transmitted wave amplitudes. Modulation depth can be characterized in terms of fringe visibility, which is defined as the ratio $(I_{max}-I_{min})/(I_{max}+I_{min})$, where $I_{max}$ and $I_{min}$ are the intensities of interference maxima and minima.

In the following a brief description is given of the dependency of these parameters on the particle size.

For particles smaller than the wavelength, the field amplitude changes with particle size raised to the third power. Since both $I_{max}$ and $I_{min}$ depend on the product between incident and scattered field amplitudes, the visibility is scaled with the third power of the size. Therefore, it is more easy to determine the particle size from the trend of the fringe visibility, since this quantity changes in a less explosive way than the way the intensity changes.

The fractional order at the centre, which is determined from the phase difference between scattered wave and transmitted wave, depends on the size of the particle B. For normal, not too small values of the refractive index step (for example, for powders in air or water) the phase change takes place for particles with diameter less than or comparable to the wavelength, typically from 100 to 1000 nm. This allows to exploit the measurement of the phase delay for metrological purposes, in a diameter range which is accessible only with difficulty for all conventional techniques of particle sizing.

In case the particle is negligibly small with respect to the wavelength of the wave IW (Rayleigh limit) the emergent spherical wave SW, which is known as scattered wave, is in phase with the incident plane wave IW, and therefore with the transmitted plane wave TW as well.

Due to the phase relation between the two waves SW and TW, which causes the two waves to sum in phase at the centre of the fringe system, the central fringe has an intensity maximum.

With increasing size of the particle B, the scattered wave SW has a phase delay with respect to the incident wave. Such phase delay depends on the product between the particle diameter and the refractive index difference $n_A-n_B$, i.e. on the optical thickness of the particle. In case the refractive index step is considerable, and in the limit where the particle has a size greater than the wavelength, the phase of the wave SW emitted by the particle is delayed by a quarter wavelength with respect to the transmitted wave TW.

For particles with intermediate diameter the phase delay takes all intermediate values.

In principle, the measurement of the scattered wave amplitude and of the phase delay between scattered wave SW and transmitted wave TW based on the interference pattern is sufficient for determining the particle size in a size range which is broader than with the traditional techniques. The conceptual scheme now described, which provides for the use of a plane wave, has still some drawbacks: 1) the specific power which strikes the particle, and consequently also the scattered power, is very low; 2) the fringe visibility depends on the distance between particle and detection plane, and decreases with increasing of such distance; 3) the detection of a great number of interference fringes requires the determination of a great number of intensity values with a high spatial frequency. Therefore, detectors with multiple sensitive elements (for example, CCD or CMOS sensors) are necessary which record a great quantity of data, which must be subsequently processed.

In order to overcome such difficulty, the present invention makes use of an optical scheme as described with reference to FIG. 1b, which provides for focusing the incident beam IW in the region where the particle B to be analysed is located. In such way the specific power which strikes the particle increases with respect to the case of incident plane wave.

Furthermore, since the amplitude of the transmitted wave TW decreases in the same way as the scattered wave SW, unlike the case of plane wave, the fringe visibility does not change with the distance from the particle.

Furthermore, due to the almost perfect matching of the transmitted and scattered wavefronts TW and SW, the interference between the two waves gives rise to intensity modulations which persist on wide fractions of the transmitted beam. This makes possible to catch the features of the interference pattern which allow to characterize the particle properties by using sensors with few elements (for example, quadrant sensors). Finally the signal collection can be carried out even at distances where the interference pattern spreads out (without contrast reduction) on wide areas, for example of the order of the centimeter. This allows for the use of high power beams (without problems of sensor saturation) and therefore to obtain even very high photocurrent signals, and this makes possible to reduce considerably the shot noise, which is the final detection limit.

Using a convergent beam involves the necessity of considering additional phenomena which play a very important role in determining morphology and amplitude of the interference fringes. The phenomenon is that of the phase anomaly, namely the Gouy effect. Due to said phenomenon a convergent beam of the TEM00 type (i.e. a Gaussian beam) undergoes a phase shift equal to half wavelength during the propagation along a path having length $z_R = \pm \pi w_0^2/\lambda$ about the position of minimum diameter $D=2w_0$ located at $z=0$.

Due to this effect it follows that whereas in the case of plane wave the phase difference between scattered wave and transmitted wave does not depend on the position of the particle, in case of a focused beam such phase difference depends in a crucial way on the position of the particle in the focal zone.

Therefore, whereas in the case of plane wave a very small particle emits a scattered wave in phase with the plane wave and thus has an intensity maximum in the direction of propagation of the plane wave, the same particle located on the optical axis z in the plane of minimum diameter scatters a wave perfectly cophasal, but in phase quadrature with the transmitted beam, and therefore the intensity of the transmitted beam is unchanged with respect to the case with no particle (see point O in FIG. 1b).

However, if the particle is displaced along a diameter onto the edge of the focal spot, for example upwards, the scattered spherical wave is slightly skew with respect to the transmitted beam and is summed in counterphase in the upper part of the transmitted beam (see point P in FIG. 1b) and in phase in the lower one (see point Q in FIG. 1b), thereby giving rise to an intensity change in excess and in defect respectively (with respect to the case with no particle) in two opposite regions along the displacement direction of the particle. This is further illustrated in the FIG. 2a. The box in the left side of FIG. 2a illustrates a simulation of an intensity distribution detected on a plane located at a distance of 135 mm from the particle B, in the case of a particle having a diameter equal to 100 nm and being struck by a beam having a diameter equal to 20 μm and a wavelength equal to 633 nm. The particle is vertically located above the optical axis z, with a distance equal to 6 μm. The centre of the box of FIG. 2a coincides with the intersection O of the optical axis z with the detection plane. In the right side of FIG. 2a the vectors of the transmitted field and the scattered field in three distinct points of the pattern illustrated in the left side, P, O, and Q respectively (according to the notation used in FIG. 1b) are shown.

Naturally, as the particle diameter changes, it is to be considered in detail the continuous and gradual change of both the scattering amplitude (which leads to visibility changes) and, above all, the phase changes between the field locally incident on the particle and the scattered spherical wave.

It is to be noted that due to the Gouy effect, for particles which are large with respect to the wavelength of the incident radiation (diffractive limit) the phase of the spherical wave scattered by a particle exactly on the optical axis is in phase opposition with the incident field. Therefore, whereas in the case of a very small particle on the optical axis no intensity change is observed from the flat hue which is observed with no particle, here strong intensity changes are observed which are distributed on the entire front and are caused by the destructive interference between scattered spherical wave and transmitted wave.

If a particle having a large diameter with respect to the wavelength of the incident radiation is displaced from the optical axis, the two wavefronts are slightly skew, as in the preceding case, but this gives mainly rise to an almost homogeneous intensity change on the entire angle of the transmitted wavefront, with only slight asymmetries of the type previously described. This is further illustrated in the FIG. 2b. The box in the left side of FIG. 2b illustrates a simulation of an intensity distribution detected on a plane in the same conditions as FIG. 2a, in the case of a particle having a diameter equal to 2000 nm. In the right side of FIG. 2b the vectors of the transmitted field and the scattered field in three distinct points of the pattern illustrated in the left side, P, O, and Q respectively (according to the notation used in FIG. 1b) are shown.

The intensity change which is caused by the phenomenon of interference between transmitted field and scattered field is proportional to the amplitude of the field scattered by the particle. In the case of particles much larger than the wavelength, wherein the phase difference with respect to the incident wave does not change as the diameter changes, this allows to determine the size of the particle.

All cases relating to particles having intermediate diameter represent a continuous variation between the two above illustrated cases. The conceptual scheme here proposed is intended to measure the asymmetry values due to the passage of a particle through the minimum diameter region of the beam, in order to simultaneously determine the phase difference between incident wave and scattered wave and the amplitude of the scattered wave in the interference pattern.

Therefore, an object of the present invention is a method of measuring properties of particles having the features defined in claim 1.

The present invention exploits the above described phenomena in order to determine the phase difference between transmitted wave and scattered wave and the amplitude of the wave scattered by a particle passing through the minimum diameter region of the beam. The particles are therefore conveyed through the exploring beam, and the asymmetry of the interference pattern and the intensity change with respect to the case with no particle are recorded as a function of time. The phase difference between scattered wave and incident wave and the amplitude of the scattered wave are therefore determined from the time sequence of such values.

The possibility provided by the present invention to verify whether the particle has crossed the beam in diametrical position in such a way to know the luminous power striking it, is of fundamental importance for metrological purposes. Since the measurement of the asymmetry in the intensity distribution of the interference pattern depends on the position of the particle with respect to the optical axis, in case a particle passes vertically through the beam and crosses exactly the optical axis the interference pattern will be always symmetrical in a horizontal direction. On the contrary, when the particle passes vertically but in a position outside the optical axis the interference pattern will have an asymmetry which is greater as the distance from the optical axis gets greater. This implies that only horizontally symmetrical interference patterns correspond to diametrical transits through the beam in which the particle has been struck by a determined power.

By using a sensor which simultaneously determines vertical and horizontal asymmetry of the interference patterns, it is possible to know the position of transit of the particle from the same data (validation procedure).

A further object of the invention is an apparatus for carrying out a method of measuring properties of particles according to the invention.

Further characteristics and advantages of the invention will become clear from the ensuing detailed description given by way of non-limiting example, with reference to the appended drawings in which:

FIGS. 1a and 1b are schemes which illustrate the principle on which the present invention is based;

FIGS. 2a and 2b illustrate simulations of interference patterns which can be generated with the optical scheme illustrated in FIG. 1b;

FIG. 3 is a schematic (and not in scale) side elevation view of an embodiment of an apparatus for carrying out a method of measuring according to the invention;

FIG. 4 is a schematic front view of a sensor which can be advantageously used for realizing an apparatus according to the invention (quadrant sensor)

FIG. 3 illustrates a schematic example of an apparatus by means of which measurements on particles can be carried out according to the invention.

Figure 1B:
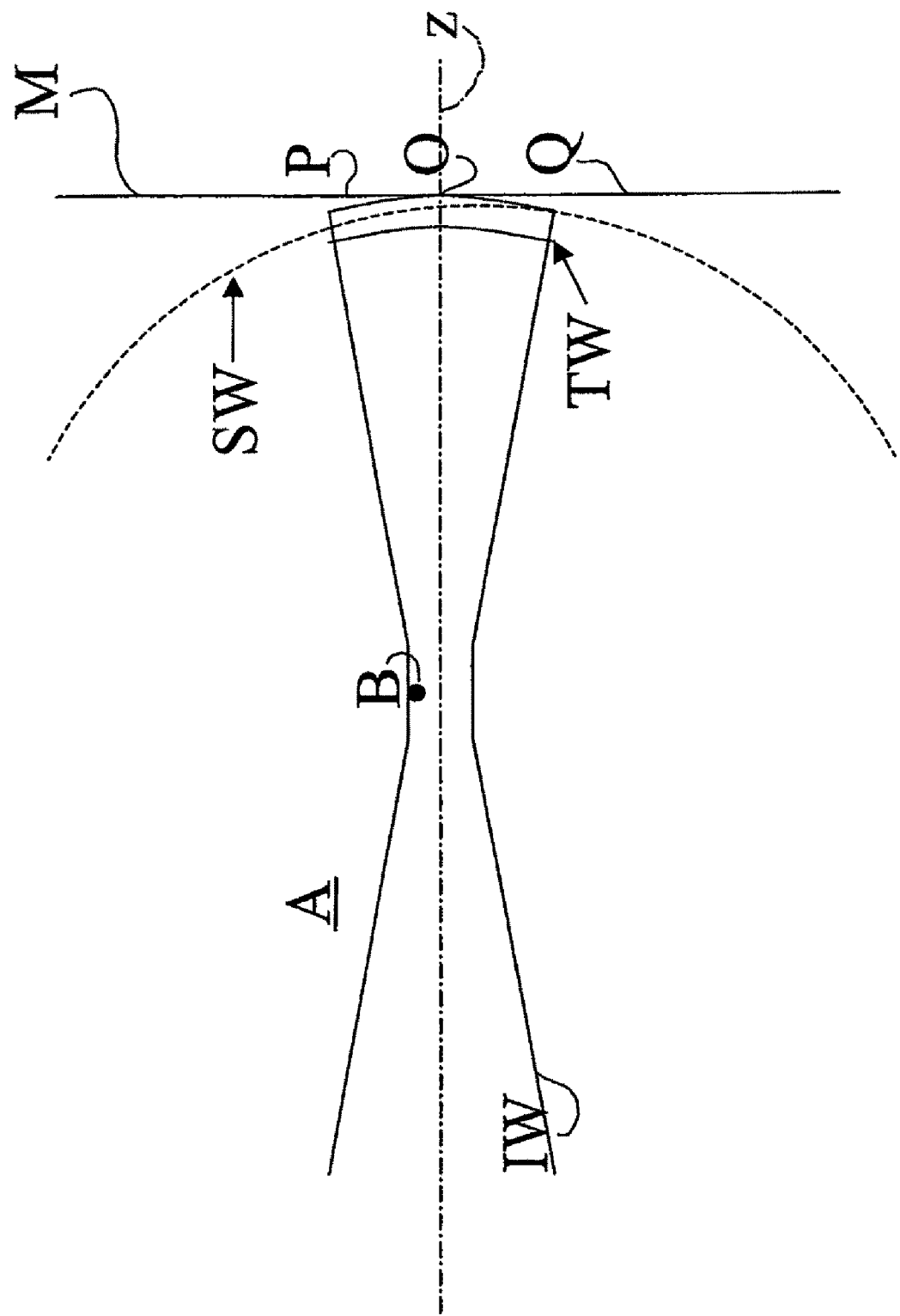

With reference to such figure, the apparatus comprises an electromagnetic radiation source 1 suitable for producing a beam of radiation IW which has a range of frequencies centred about a predetermined frequency $\omega$, corresponding to a wavelength of $\lambda$ in a vacuum. Downstream of the source 1 along the propagation direction z of the beam, there are optionally but not necessarily a spatial filter (not shown) and beam shaping optics 2.

The source 1 preferably emits visible or infra-red light and is constituted, for example, by a light-emitting diode or by a semiconductor laser or a laser of another type, according to measurement requirements. In general, the use of sources of radiation with a band that is not too narrow appreciably reduces effects due to spurious or multiple interference. For some applications, the source may advantageously emit radiation distributed around several wavelength values (an arrangement known as a "multi-coloured source").

The particles B to be analyzed may be composed of any solid or fluid substance, material or element (powders, aerosols, drops, bubbles, cells). The particles pass through the exploring beam (according to the direction of arrow S), being transported by the medium A or by fall, floatation or by their own motion or in any other way they can move within a region MR illuminated by the beam IW. The medium A may be solid or fluid but in any case must be transparent to the frequency/ies of the incident radiation used.

For particles B which are dispersed in a fluid medium A, a suitable conventional method of confinement ensures that only one particle at a time is present in the observation region MR struck by the beam IW. The observation region MR through which the particles B are conveyed has a width d along the direction z of the beam IB which is thin enough to allow a single particle B at a time to pass through the region MR. For reasons concerning the measurement of the phase difference, in order to avoid ambiguities deriving from the phase anomaly it is advantageous that the particles pass through the beam in the vicinity of the minimum diameter region. Such condition can be obtained for example by focusing the beam in such a way that the Rayleigh region $Z_R$ has a greater or much greater length than the thickness of the region MR through which the particles are conveyed. This condition corresponds also to the fact that the beam size in the minimum diameter region is much greater than the wavelength, as required also by the fact that the beam must be capable to illuminate in a uniform way particles having greater size than the wavelength.

A device 3 for collecting and recording the radiation coming from the observation region MR is aligned on the propagation direction z of the radiation IW (that is, on the optical axis of the system) and is disposed on a plane M located at a distance $z_m$. The detected radiation comprises scattered radiation produced by the scattering interaction of the incident radiation IW with the particle B in accordance with the principle described above and a portion TW formed by a fraction of the incident beam IW which is transmitted undisturbed through the observation region MR. The device 3 is formed by a plurality of sensor elements which can detect a plurality of electromagnetic radiation intensity values, and which are disposed in the plane M.

Preferably, the device 3 is constituted by a quadrant sensor (see also FIG. 4) which is struck by the most part of the beam radiation and whose centre O is positioned on the optical axis z of the system. Said quadrant sensor is subdivided into four sectors A1, B1, C1, and D1 which have sensitive areas preferably constituted by photodiodes (for example, silicon photodiodes). The four sensors are arranged in the plane M in a manner such as to define a pair of reciprocally perpendicular axes x, y, which intersect each other at the centre O of the device 3 and form the borders of the quadrants. The axis x is disposed parallel to the projection of the transit direction of the particle on the detection plane M. Alternatively, CMOS devices with a great number of sensitive elements can be advantageously used in embodiments wherein the analysis of only four intensity values is not sufficient.

The apparatus described above allows to measure the asymmetries of the intensity distribution as a function of time and in two directions perpendicular each other, one being substantially parallel and the other being substantially perpendicular to the transit direction of the particles.

Advantageously, the use of a quadrant sensor allows to measure with a great precision the weak asymmetry of the intensity distribution in the pattern of interference between scattered wave and transmitted wave, making it possible to simultaneously carry out a validation procedure of the single signals in relation to the position of the particle through the beam, as will be further illustrated in the following.

Means (not shown) for obtaining, in the device 3, a suitable distribution of the radiation are optionally interposed between the particle to be analyzed and the sensor device 3. These means may be constituted, for example by an optical system.

The sensitive elements of the sensor device 3 detect a plurality of radiation intensity values, one for each of the sensitive elements, and supply corresponding signals to a processing unit (not shown) which are substantially proportional to the detected intensity. In the case of quadrant sensor the four signals supplied by the sensor 3 will be designated in the following with the letter which identifies the corresponding sectors, A1, B1, C1, D1, as shown in FIG. 4.

The processing unit is programmed to determine the size of the particles by analysis of the asymmetries defined by the measured radiation intensity values, and by analysis of the amplitude scattered by the particle. Furthermore, it is also programmed to select the signals corresponding to those particles which have diametrically passed through the beam, crossing it substantially at the optical axis z. It can also be programmed to determine the transit distance from the optical axis in such a way to normalize the wave amplitude value which has been measured in a non-central portion of the beam with respect to the diametrical transit condition.

An example of a method of processing the data collected in a measurement performed by apparatus as described above or in another foreseeable embodiment consists of the following steps (let's assume that the transit direction of the particle is such as that an asymmetry is produced between the upper portion of the device 3 formed by the sectors A1 and B1 and the lower portion formed by the sectors C1 and D1, i.e. a vertical transit direction):

a) recording, at a fixed distance $z_m$ from the region MR, four intensity values coming from the corresponding quadrants of the sensor 3, which will be designated with A1, B1, C1, D1 in the following;

b) recording a suitable set of intensity values measured by the four quadrants with a sampling frequency such as that it is possible to determine for each single particle the trend of the asymmetry induced by it as a function of time;

c) processing the data obtained for the ith generic record in order to obtain a sequence of asymmetry values $a_i=(A1+B1)-(C1+D1)$ and a sequence of values $p_i=A1+B1+C1+D1$ of power incident on the sensor as a function of time (i designates the generic value of a and p calculated on the basis of data A1, B1, C1, D1 relating to the ith record);

d) processing the data obtained for the ith generic record in order to obtain a sequence of asymmetry values $v_i=(A1+C1)-(B1+D1)$ as a function of time (i designates the generic value of v calculated on the basis of data A1, B1, C1, D1 relating to the ith record);

e) processing the data relating to sequence $v_i$ in terms of the crossing distance of the particle from the optical axis of the system;

f) selecting the events corresponding to a substantially diametrical transit;

g) processing the data relating to sequences $a_i$ and $p_i$, selected at step f) for the sole substantially diametrical transits, in terms of the power removed from the beam and of the phase delay between scattered wave and transmitted wave in order to determine the size of the particle.

In addition to the method described above, it is possible to integrate the processing with the following step, which can be followed for example by step g) or suitable variations: f') processing the data relating to sequence $v_i$ in order to determine the crossing distance and subsequently normalize the signal due to the smaller specific power which struck the particle.

Figure 5A:
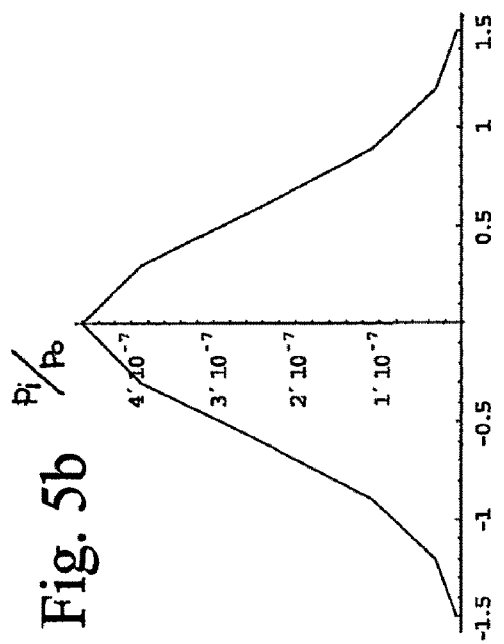
FIGS. 5a, 5b, 5c and 5d are diagrams which illustrate the normalized asymmetry and the normalized intensity integral as a function of the position of particles having diameter equal to 100 nm and 2000 nm.
Figure 5B:
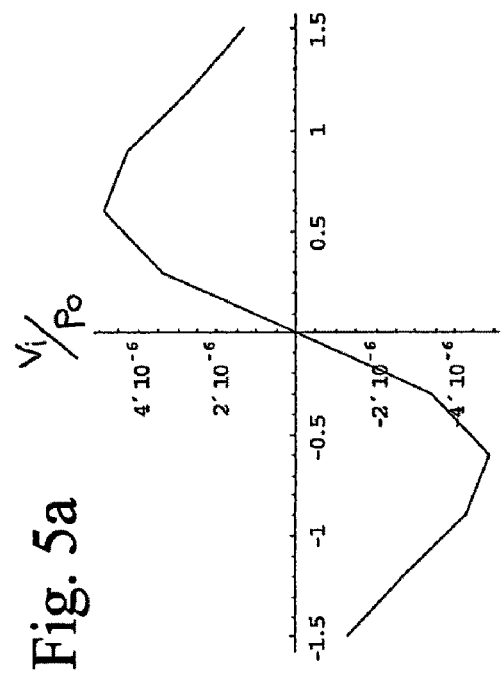
Figure 5C:
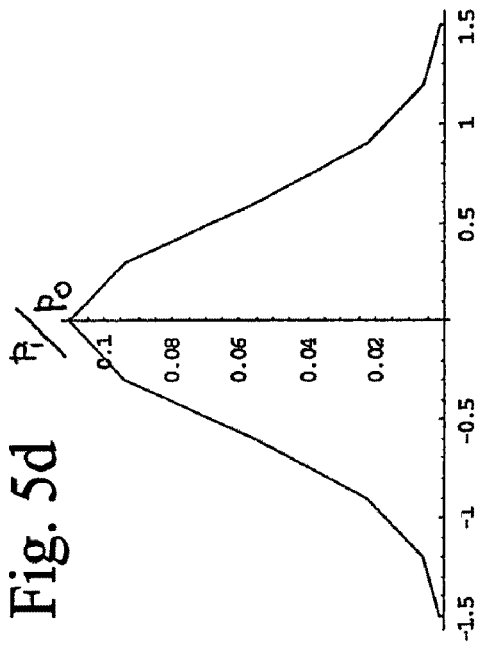
Figure 5D:
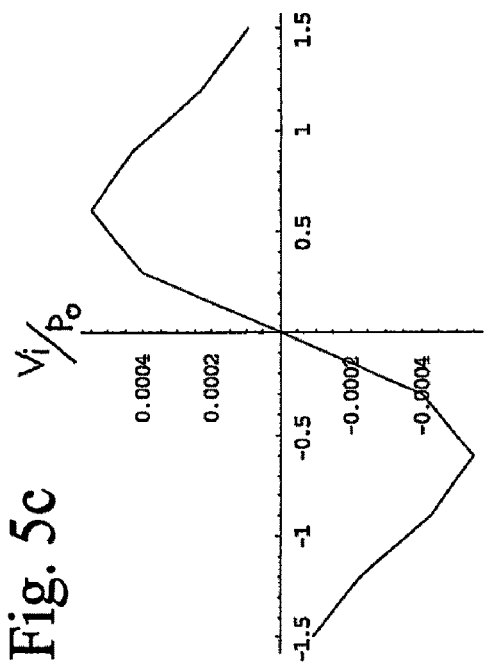

As an example, FIGS. 5a, 5b, 5c and 5d show diagrams which illustrate the trend of the asymmetry $v_i$ and of the intensity integral $p_i$ as a function of the position of the particle within the observation region MR, in the case of a diametrical transit. The values are normalized to the intensity integral $p_0$ (i.e. A1+B1+C1+D1) with no particle. The particle distance from the optical axis located at the origin of the axes is defined in abscissa and in arbitrary units. The diagrams of FIGS. 5a and 5b have been calculated for a particle having a diameter equal to 100 nm, whereas the diagrams of FIGS. 5c and 5d have been calculated for a particle having a diameter equal to 2000 nm. The incident beam has a wavelength equal to 633 nm and a diameter equal to 20 μm, and the sensor is located at a distance $z_m$ from the observation region MR equal to 135 mm.

The methods described above, as well as other possible embodiments of the present invention, may require a large number of acquisitions, for example, to be able to reduce the noise which inevitably afflicts the measurement and thus to obtain an adequate determination of the properties of the particles under examination.

The invention is not intended to be limited to the embodiments described and illustrated herein which should be considered as examples of the implementation of the method and of the corresponding apparatus; rather, the invention may undergo modifications relating to the shape, construction and arrangement of parts, constructional details, and data-acquisition and data-analysis methods.

Moreover, the invention may be used for the measurement of the properties of materials which can be deduced by measurement of the scattered wave amplitude and of the phase delay between the scattered waves and the transmitted wave as described above, in accordance with possible variants which will seem appropriate to persons skilled in the art and which should be understood as being included within the scope of the invention as defined in the appended claims.

The invention claimed is:

1. A method of measuring properties of particles, comprising the steps of:
   generating a beam of radiation which is propagated along an optical axis;
   illuminating with the beam an observation region which is transited by a particle, a portion of the beam giving rise to radiation which is scattered by scattering interaction of the portion of the beam with the particle, and another portion being transmitted substantially undisturbed along the optical axis through the observation region; and
   detecting, in a detection plane disposed along the optical axis, a plurality of radiation intensity values which are determined by the interference between the scattered radiation and the transmitted radiation;
   wherein said detection of the radiation intensity values in the detection plane is carried out according to a time sequence of acquisitions corresponding to successive transit positions of said particle through the observation region, and
   wherein on the basis of said time sequence of acquisitions, the trend of a parameter of asymmetry of the distribution of the plurality of radiation intensity values with respect to the optical axis, due to the successive transit positions of the particle, is determined as a function of time,
   depending on the trend of the parameter of asymmetry which has been determined as a function of time, the trends of phase delay and amplitude of the scattered radiation with respect to the transmitted radiation are determined as a function of time, and
   the properties of the particle are determined on the basis of the trends of the phase delay and amplitude of the scattered radiation as a function of time.

2. A method according to claim 1, wherein the radiation beam is focused in such a way so that its minimum diameter region is disposed in the vicinity of the observation region.

3. A method according to claim 2, wherein the observation region is disposed within the Rayleigh zone of said beam, the radiation beam being focused so that the extent of the Rayleigh zone is greater than the width of the observation region in the direction of the optical axis.

4. A method according to claim 1, wherein said detection of the radiation intensity values in the detection plane is carried out in such a way to measure one value of radiation intensity detected as a whole by each of four quadrants of the detection plane, said quadrants being defined by a pair of reciprocally perpendicular axes which intersect each other at the optical axis, one of said axes being disposed parallel to the projection of the transit direction of the particle on the detection plane.

5. A method according to claim 4, wherein the asymmetry parameter is determined by comparing the values of radiation intensity detected as a whole by the corresponding quadrants in the same acquisition.

6. A method according to claim 5, wherein the determination of the trends of phase delay and amplitude of the scattered radiation with respect to the transmitted radiation is carried out selectively in the case of the trend of the asymmetry parameter determined as a function of time corresponding to a substantially diametrical transit of the particle.

7. Apparatus arranged for implementing a measurement method according to claim 1, comprising:
- a source of the radiation beam, suitable for illuminating the observation region;
- a sensor disposed on the detection plane and along the optical axis in a manner to detect simultaneously a plurality of radiation intensity values determined by the interference between the scattered radiation and the transmitted radiation and to make available a signal indicative of the detection, said detection of the radiation intensity values in the detection plane being carried out according to a time sequence of acquisitions corresponding to successive transit positions of the particle through the observation region; and
- a processor adapted to process said signal, the processor being programmed to:
  - determine, on the basis of said time sequence of acquisitions, the trend of a parameter of asymmetry of the distribution of the plurality of radiation intensity values with respect to the optical axis, due to the successive transit positions of the particle, as a function of time,
  - determine, depending on the trend of the parameter of asymmetry which has been determined as a function of time, the trends of phase delay and amplitude of the scattered radiation with respect to the transmitted radiation as a function of time, and
  - determine the properties of the particle on the basis of the trends of the phase delay and amplitude of the scattered radiation as a function of time.

8. Apparatus according to claim 7, wherein said sensor comprises a quadrant sensor comprising a sensitive surface subdivided into four quadrants which are adapted to detect respective values of said plurality of radiation intensity values, said quadrants being delimited by a pair of reciprocally perpendicular axes which intersect each other at the optical axis, one of said axes being disposed parallel to the projection of the transit direction of the particle on the detection plane.

9. Apparatus according to claim 8, wherein said processor is programmed to determine the asymmetry parameter by comparing the values of radiation intensity detected as a whole by the corresponding quadrants in the same acquisition.

10. Apparatus according to claim 9, wherein said processor is programmed to determine the trends of phase delay and amplitude of the scattered radiation with respect to the transmitted radiation selectively in the case of the trend of the asymmetry parameter determined as a function of time corresponding to a substantially diametrical transit of the particle.

* * * * *